United States Patent
Koike et al.

(10) Patent No.: US 7,857,862 B2
(45) Date of Patent: Dec. 28, 2010

(54) ONE-PART HAIR DYE COMPOSITION

(75) Inventors: Kenzo Koike, Tokyo (JP); Atsuko Ebato, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 12/303,604

(22) PCT Filed: Jun. 7, 2007

(86) PCT No.: PCT/JP2007/000612

§ 371 (c)(1),
(2), (4) Date: Dec. 5, 2008

(87) PCT Pub. No.: WO2007/141918

PCT Pub. Date: Dec. 13, 2007

(65) Prior Publication Data

US 2010/0037404 A1 Feb. 18, 2010

(30) Foreign Application Priority Data

Jun. 7, 2006 (JP) .............................. 2006-159152

(51) Int. Cl.
*A61Q 5/10* (2006.01)
(52) U.S. Cl. ............... 8/405; 8/435; 8/574; 8/581; 8/604; 8/611; 8/632; 8/670
(58) Field of Classification Search ............ 8/405, 8/435, 574, 581, 604, 611, 632, 670
See application file for complete search history.

(56) References Cited

U.S. PATENT DOCUMENTS

| | | | |
|---|---|---|---|
| 4,208,183 A | 6/1980 | Grollier et al. | |
| 4,900,326 A | 2/1990 | Grollier | |
| 5,021,067 A * | 6/1991 | Grollier | 8/409 |
| 5,704,949 A | 1/1998 | Prota et al. | |
| 7,083,655 B2 | 8/2006 | Pratt et al. | |
| 2006/0000032 A1 | 1/2006 | Knuebel et al. | |

FOREIGN PATENT DOCUMENTS

| | | |
|---|---|---|
| CN | 1599590 A | 3/2005 |
| DE | 10120915 A1 | 11/2001 |
| EP | 0 533 937 A1 | 3/1993 |
| EP | 1 254 650 A2 | 11/2002 |
| EP | 1 430 873 A1 | 6/2004 |
| EP | 1433470 A1 | 6/2004 |
| JP | 57-192310 A | 11/1982 |
| JP | 8-32618 | 3/1996 |
| JP | 11-12139 | 1/1999 |
| JP | 2002-322038 | 11/2002 |
| JP | 2003-055175 | 2/2003 |
| JP | 2003-342139 | 12/2003 |
| WO | WO 92/14441 A1 | 9/1992 |
| WO | WO 99/66890 A1 | 12/1999 |
| WO | WO 2004/024109 A1 | 3/2004 |

OTHER PUBLICATIONS

STIC Search Report dated Mar. 8, 2010.*
Patent Abstracts of Japan, English language abstract of JP 57-192310, Nov. 26, 1982 (listed on accompanying PTO/SB/08A as document FP1).
Dialog Database, Derwent World Patent Index File 351 Accession No. 6077403, English language abstract for WO 1992/014441 A1, published Sep. 3, 1992 (listed on accompanying PTO/SB/08A as document FP2).
Dialog Database, Derwent World Patent Index File 351 Accession No. 10376798, English language abstract for WO 1999/066890 A1, published Dec. 29, 1999 (listed on accompanying PTO/SB/08A as document FP4).
Dialog Database, Derwent World Patent Index File 352 Accession No. 2002-076390/200211, English language abstract for DE 10120915 A1, Nov. 15, 2001 (listed on accompanying PTO/SB/08A as document FP5).
Dialog Database, Derwent World Patent Index File 351 Accession no. 14485871, English language abstract for WO 2004/024109 A1 (listed on accompanying PTO/SB/08A as document FP7), (2004).
Dialog Database, Derwent World Patent Index File 352 Accession No. 2004-490110/200447, English language abstract for EP 1433470 A1, Jun. 30, 2004 (listed on accompanying PTO/SB/08A as document FP8).
International Search Report for International Application No. PCT/JP2007/000612, mailed on Jul. 10, 2007, Japanese Patent Office, Tokyo, Japan.

(Continued)

*Primary Examiner*—Eisa B Elhilo
(74) *Attorney, Agent, or Firm*—Sterne, Kessler, Goldstein & Fox P.L.L.C.

(57) ABSTRACT

A one-part hair dye composition containing (A) one or more compounds represented by the formula (1), (B) a silicone, and (C) a polyol, wherein the composition has a pH of from 8 to 11,

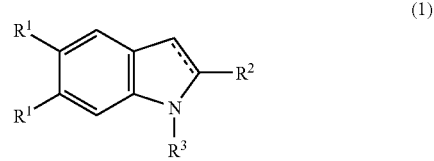

(1)

wherein, a broken line represents the presence or absence of π bond, $R^1$ represents OH or acetoxy, $R^2$ represents H, —COOR (R representing H, $CH_3$ or $C_2H_5$) or —COO$^-$X$^+$ ($X^+$ representing a cation), and $R^3$ represents H, acetyl, $CH_3$ or $C_2H_5$.

6 Claims, No Drawings

OTHER PUBLICATIONS

Koike et al., U.S. Appl. No. 12/303,607 (Natl. Phase of PCT/JP2007/000613; Int'l Filing Date: Jun. 7, 2007).

Koike et al., U.S. Appl. No. 12/303,610 (Natl. Phase of PCT/JP2007/000614; Int'l Filing Date: Jun. 7, 2007).

Dialog Database, Derwent World Patent Index File 351 Accession No. 4239691, English language abstract for JP 08-32618 (JP 1996032618), published Mar. 29, 1996 (listed on accompanying PTO/SB/08A as document FP9).

Dialog Database, JAPIO, file 347 Accession No. 7453523 and Derwent World Patent Index File 351 Accession No. 50010220, English language abstract and patent family for JP 2002-322038, published Nov. 8, 2002.

Dialog Database, Derwent World Patent Index File 351 Accession No. 9688038, English language abstract for JP 11-012139, published Jan. 19, 1999.

Dialog Database, Derwent World Patent Index File 351 Accession No. 14034115, English language abstract for JP 2003-342139 A, published Dec. 3, 2003.

Office action for CN 200780020625.2 (which corresponds to U.S. Appl. No. 12/303,607), mailed Jul. 16, 2010 from the Patent Office of the People's Republic of China, Beijing, China.

International Preliminary Report on Patentability including the Written Opinion for PCT/JP2007/000612 (the PCT phase of U.S. Appl. No. 12/303,604), issued Jan. 13, 2009 by the International Bureau of WIPO, Geneva, Switzerland.

USPTO Office action for U.S. Appl. No. 12/303,607, mailed Apr. 5, 2010, and reply thereto filed Aug. 18, 2010.

USPTO Office action for U.S. Appl. No. 12/303,610, mailed May 13, 2010, and reply thereto filed Aug. 18, 2010.

International Preliminary Report on Patentability including the Written Opinion for PCT/JP2007/000613 (the PCT phase of U.S. Appl. No. 12/303,607), issued Jan. 13, 2009 by the International Bureau of WIPO, Geneva, Switzerland.

International Preliminary Report on Patentability including the Written Opinion for PCT/JP2007/000614 (the PCT phase of U.S. Appl. No. 12/303,610), issued Jan. 13, 2009 by the International Bureau of WIPO, Geneva, Switzerland.

\* cited by examiner

ONE-PART HAIR DYE COMPOSITION

FIELD OF THE INVENTION

The present invention relates to an air-oxidative one-part hair dye composition excellent in dyeing properties, hair feel after treatment and usability.

BACKGROUND OF THE INVENTION

Air-oxidative hair dye compositions using a melanin precursor such as indoles or indolines have conventionally been known (refer to, for example, Patent Documents 1 to 3). These hair dye compositions however do not have sufficient dyeing properties.
Patent Document 1 JP-B-8-32618
Patent Document 2 JP-A-2003-55175
Patent Document 3 JP-A-2002-322038

DISCLOSURE OF THE INVENTION

The present invention provides a one-part hair dye composition, having a pH of from 8 to 11, containing the following components (A) to (C):
(A) one or two or more compounds represented by the following formula (1):

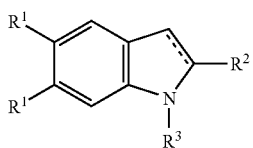

(1)

wherein, a broken line represents the presence or absence of a π bond, $R^1$ represents a hydroxyl or acetoxy group, $R^2$ represents a hydrogen atom, —COOR(R representing a hydrogen atom, methyl group or ethyl group) or —COO$^-$X$^+$ (X$^+$ representing a cation), and $R^3$ represents a hydrogen atom, acetyl group, methyl group or ethyl group,
(B) a silicone, and
(C) a polyol.

MODE FOR CARRYING OUT THE INVENTION

The present invention relates to an air-oxidative hair dye composition excellent in dyeing properties, hair feel after treatment and usability.
The present inventors have found that the above-described problem can be overcome by adding a silicone and a polyol to an air-oxidative hair dye composition using a melanin precursor.
The compound as Component (A) represented by the formula (1) is an indole or indoline derivative (melanin precursor) which is converted to a melanin pigment by oxidation. Examples of the compound represented by the formula (1) include 5,6-hydroxyindole, 5,6-dihydroxyindole-2-carboxylic acid, 5,6-dihydroxyindoline and 5,6-dihydroxyindoline-2-carboxylic acid. These compounds may be used either singly or in combination of two or more, but combined use of two or more of them enables to control the final hair color. It is preferred to use 5,6-hydroxyindole and 5,6-dihydroxyindole-2-carboxylic acid in combination from the viewpoint of dying hair into a natural color tone. A molar ratio of 5,6-hydroxyindole to 5,6-dihydroxyindole-2-carboxylic acid, when they are used in combination, is preferably from 50:50 to 999:1, more preferably from 80:20 to 99:1. Amounts of 5,6-hydroxyindole and 5,6-dihydroxyindole-2-carboxylic acid can be determined by reverse phase HPLC.

The total content of the compounds as Component (A) in the hair dye composition of the present invention is preferably from 0.05 to 5 wt. %, more preferably from 0.1 to 2 wt. % from the viewpoints of dyeing properties and economy.

In order to improve the conditioning effects and dyeing properties of the hair dye composition of the present invention, a silicone is incorporated therein as Component (B). In the present invention, one or more silicones can be used. Examples of the silicone include dimethylpolysiloxanes, polyether-modified silicones, amino-modified silicones, carboxy-modified silicones, methylphenylpolysiloxanes, fatty acid-modified silicones, alcohol-modified silicones, aliphatic alcohol-modified silicones, epoxy-modified silicones, fluorine-modified silicones, cyclic silicones and alkyl-modified silicones. Of these, dimethylpolysiloxanes, polyether-modified silicones and amino-modified silicones are preferred. Dimethylpolysiloxanes can give good lubrication to hair, polyether-modified silicones can give smoothness to hair, and amino-modified silicones give moisturized feel to hair. It is preferred to use, of these silicones, two or more silicones selected from the group consisting of dimethylpolysiloxanes (having a number average polymerization degree of less than 1000), dimethylpolysiloxanes (having a number average polymerization degree of 1000 or greater) and amino-modified silicones. When they are used in combination, it is preferred to adjust the weight ratio of a dimethylpolysiloxane (having a number average polymerization degree of less than 1000) to a dimethylpolysiloxane (having a number average polymerization degree of 1000 or greater) to from 10:90 to 99:1, more preferably from 50:50 to 95:5; a weight ratio of a dimethylpolysiloxane (having a number average polymerization degree of less than 1000) to an amino-modified silicone to from 5:95 to 95:5, more preferably 10:90 to 90:10; a weight ratio of a dimethylpolysiloxane (having a number average polymerization degree of 1000 or greater) to an amino-modified silicone to from 1:99 to 95:5, more preferably from 10:90 to 90:10; and a weight ratio among a dimethylpolysiloxane (having a number average polymerization degree of less than 1000), a dimethylpolysiloxane (having a number average polymerization degree of 1000 or greater) and an amino-modified silicone to 10:1 to 100:1 to 100, more preferably 10:1 to 10:1 to 10. Moreover, they are used in combination so that the nitrogen content derived from the amino-modified silicone in the total amount of the silicones falls within a range from 0.01 to 0.7 wt. %, more preferably from 0.05 to 0.5 wt. % from the viewpoint of affinity to the hair.

The Dimethylpolysiloxane is represented by the following formula (b1):

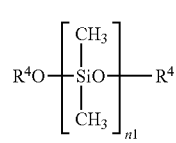

(b1)

wherein, $R^4$ represents $Si(CH_3)_3$ or a hydrogen atom, and $n^1$ stands for a number from 3 to 20000.

Examples of the commercially available dimethylpolysiloxane (having a number average polymerization degree of less than 1000) include "SH200" series (such as "SH200 C Fluid 1CS", "SH200 C Fluid 2CS", "SH200 C Fluid 5S", "SH200 C Fluid 10CS", "SH200 C Fluid 20CS", "SH200 C Fluid 30CS", "SH200 C Fluid 50CS", "SH200 C Fluid 100CS", "SH200 C Fluid 200CS", "SH200 C Fluid 350CS", "SH200 C Fluid 500CS", "SH200 C Fluid 1,000CS", "SH200 C Fluid 5,000CS", "SH200 Fluid 1.5CS", "SH200 Fluid 3,000CS", "SH200 Fluid 10,000CS", "SH200 Fluid 12,500CS", and "SH200 Fluid 30, 000CS") (each, product of Dow Corning Toray), "TSF-451" series (product of GE Toshiba Silicone) and "KF-96" series (product of Shin-Etsu Silicone). These silicone oils in the emulsion form can also be used.

Examples of the commercially available dimethylpolysiloxane (having a number average polymerization degree of 1000 or greater) include "SH200" series (such as "SH200 Fluid 60,000CS", "SH200 Fluid 100,000CS" and "SH200 Fluid 1,000,000CS", each product of Dow Corning Toray), "TSF451-100MA" (product of GE Toshiba Silicone), "BY11-026" (a solution of a highly polymerized silicone diluted with a low-viscosity silicone; product of Dow Corning Toray), "KF9008" (a solution of a highly polymerized silicone diluted with a cyclic silicone, product of Shin-Etsu Silicone), "BY22-050A" (a cationic emulsion of a highly polymerized silicone, product of Dow Corning Toray), "BY22-060" (a cationic emulsion of a solution of a highly polymerized silicone diluted with a low viscosity silicone, product of Dow Corning Toray), "BY22-020" (a cationic emulsion of a solution of a highly polymerized silicone diluted with liquid paraffin, product of Dow Corning Toray), and "KM904" (a cationic emulsion of a solution of a highly polymerized silicone diluted with a low viscosity silicone, product of Shin-Etsu Silicone).

The term "polyether-modified silicone" is a generic name of polyoxyethylene-methylpolysiloxane copolymers and poly(oxyethylene-oxypropylene)methylpolysiloxane copolymers and examples thereof include compounds represented by the following formula (b2) or (b3):

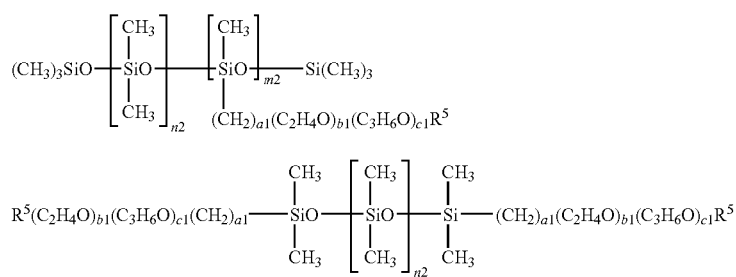

wherein, $R^5$ represents a hydrogen atom or $C_{1-12}$ alkyl group, $n^2$ is from 1 to 2000, $m^2$ is from 1 to 1000, $a^1$ is from 0 to 10, $b^1$ is from 0 to 50, and $c^1$ is from 0 to 50, with the proviso that $b^1+c^1 \geq 1$.

Examples of the commercially available polyether-modified silicone include "SH3771M", "SH3772M", "SH3773M", "SH3775M", "SH3749", "SS-2081", "SS-2802", "SS-2803", "SS-2804", and "SS-2805" (each, product of Dow Corning Toray), "KF-351A", "KF-352A", "KF-353A", "KF-354A", "KF-355A", "KF-615A", "KF-618", "KF-945A", "KF-6004", "KF-6008", "KF-6011", "KF-6012", "KF-6015", "KF-6015", "X-22-4272", "X-22-4952", and "X-22-6266" (each, product of Shin-Etsu Silicone).

As the amino-modified silicone, those having an amino or ammonium group are usable. Amino-modified silicone oils having all or a part of the terminal hydroxyl groups thereof blocked with a methyl group or the like, or amodimethicones having an unblocked terminal group are both usable. Poly(N-acylalkyleneimine)-modified silicones are also usable. Preferred examples of the amino-modified silicone include those represented by the following formula (b4) or (b5):

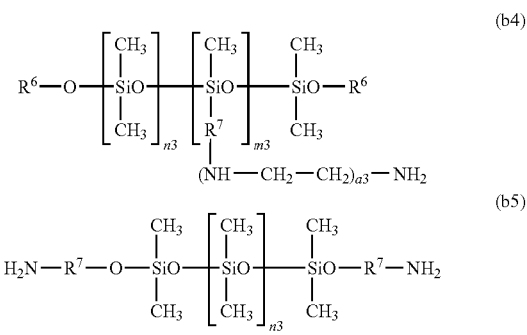

wherein, $R^6$ represents $Si(CH_3)_3$ or a hydrogen atom, $R^7$ represents a $C_{2-8}$ alkylene group, n stands for a number from 1 to 20000, $m^3$ stands for a number from 1 to 2000, $a^3$ stands for a number from 0 to 3, and a nitrogen content is preferably from 0.02 to 4 wt. %, more preferably from 0.1 to 1 wt. %.

Examples of the commercially available amino-modified silicone include amino-modified silicone oils such as "SF8451C" (having a viscosity of 600 mm²/s and a nitrogen content of 0.8 wt. %, product of Dow Corning Toray), "SF8452C" (having a viscosity of 700 mm²/s and a nitrogen content of 0.2 wt. %, product of Dow Corning Toray), "SF8457C" (having a viscosity of 1200 mm²/s and a nitrogen content of 0.8 wt. %, product of Dow Corning Toray), "KF8003" (having a viscosity of 1850 mm²/s and a nitrogen content of 0.7 wt. %, product of Shin-Etsu Silicone), "KF8005" (having a viscosity of 1200 mm²/s and a nitrogen content of 0.1 wt. %, product of Shin-Etsu Silicone), "KF867" (having a viscosity of 1300 mm²/s and a nitrogen content of 0.8 wt. %, product of Shin-Etsu Silicone), and "KF8012" (having a viscosity of 90 mm²/s and a nitrogen content of 0.6 wt. %, product of Shin-Etsu Silicone); and amodimethicone emulsions such as "SM8704C" (having a nitrogen content of 0.8 wt. %, product of Dow Corning Toray), "SM8904C" (having a nitrogen content of 0.3 wt. %, product of Dow Corning Toray) and "BY22-079" (having a nitrogen content of 0.6 wt. %, product of Dow Corning Toray). In addition, "CF1046" (having a nitrogen content of 0.14 wt. %, product of Dow Corning Toray) which is a mixture of a dimethylpolysiloxane (having a number average polymerization degree of 550), a dimethylpolysiloxane (having a number average polymerization degree of 2700) and an amino-modified silicone (weight ratio of 10:3.7:2.9) is also preferred.

The content of the silicone(s) as Component (B) in the hair dye composition of the present invention is preferably from 0.01 to 10 wt. %, more preferably from 0.05 to 6 wt. %, even more preferably from 0.3 to 3 wt. %.

As Component (C), $C_{2-20}$ polyol is usable. Specific examples of the polyol include alkylene glycols such as ethylene glycol, diethylene glycol, triethylene glycol, polyethylene glycol, propylene glycol, dipropylene glycol, 1,2-butylene glycol, 1,3-butylene glycol and hexylene glycol; glycerins such as glycerin, diglycerin and polyglycerin; sugar alcohols such as xylitol, mannitol, galactitol and sorbitol; and other polyols such as pentaerythritol and pentanediol. Of these, 1,3-butylene glycol, glycerin and dipropylene glycol are preferred.

The above-described polyol as Component (C) may be used either singly or in combination of two or more. Their content in the hair dye composition of the present invention is preferably from 0.1 to 20 wt. %, more preferably from 0.5 to 8 wt. % from the standpoints of hair feel during or after application of the composition, dyeing properties, easiness to apply and usability.

In the hair dye composition of the present invention, a polymer may be incorporated in order to improve the usability and easiness in application work. The polymer is incorporated as a thickener and may either be a nonionic or ionic polymer. Examples of the nonionic polymer include hydroxyethyl cellulose (for example, "SE-850", product of Daicel Chemical and "Cellosize HECQP52000H", product of Nagase & Co., Ltd.), sodium carboxymethylcellulose ("CMC Daicel 1220", product of Daicel Chemical), sodium hydroxyethylcellulose hydroxypropyl stearyl ether hydroxypropylsulfonate (for example, a compound described in Preparation Example 1 of JP-A-11-12139), hydroxypropylmethyl cellulose (for example, "Metolose 60SH-10000", product of Shin-Etsu Chemical), guar gum (for example, "Fiberon S", product of Dainippon Sumitomo Pharma), pullulan (for example, "Pullulan P1-20", product of Hayashibara Inc.), hydroxypropyl chitosan (for example, "Chitofilmer HV-10", product of Ichimaru Pharcos), chitosan dl-pyrrolidonecarboxylate (for example, "Chitomer PC", product of Union Carbide Corp.), polyvinylpyrrolidone ("Luviskol K-12", "Luviskol K-30", and "PVP K-120", each product of BASF), polyvinyl alcohol ("Gohsenol EG-40", product of Nippon Synthetic Chemical Industry), vinyl alcohol/vinylamine copolymer ("VA-120-HCl, product of Air Products and Chemicals), and high polymerization degree polyethylene glycol ("Polyox WSRN-60K", product of Union Carbide Japan).

Examples of the anionic polymers include polyacrylic acid ("Carbopol 941" and "Carbopol 981", each product of Noveon), acrylic acid/alkyl methacrylate copolymer ("Carbopol ETD2020", product of Noveon), hydrolysate of a lower alkyl vinyl ether/maleic anhydride copolymer partially crosslinked with a terminal-unsaturated diene compound or monoalkyl ester thereof ("Stabilize 06" and "Stabilize QM", each product of ISP), carrageenan (for example, "Soageena LX22" and "Soageena ML210", each product of Mitsubishi Rayon), xanthan gum (for example, "Echo gum T", product of Dainippon Sumitomo Pharma), welan gum (for example, "K1C376" and "K1A96", each product of Sansho), and hydroxypropyl xanthan gum (for example, "Rhaball gum EX", product of Dainippon Sumitomo Pharma).

Examples of the cationic polymer include those containing an amino group or ammonium group in the side chain of the polymer chain thereof and those containing a diallyl quaternary ammonium salt as a constituent unit, each in the form of an aqueous solution. Specific examples of them include a cationic cellulose derivative (for example, "Reoguard G" and "Reoguard GP", each product of Lion Corporation, "Polymer JR-125", "Polymer JR-400", "Polymer JR-30M", "Polymer LR-400", and "Polymer LR-30M", each product of Union Carbide, and "Celquat H-100" and "Celquat L-200", each product of National Starch & Chemicals), a cationic guar gum derivative (for example, "Juguar C-13S" and "Juguar C-17", each product of Rhodia, and "Rhaball Gum CG-M", "Rhaball Gum CG-M7", and "Rhaball CG-M8M", each product of Dainippon Sumitomo Pharma), polymers or copolymers of a diallyl quaternary ammonium salt ("Merquat 100", "Merquat 280", "Merquat 295", and "Merquat 550", each, product of Calgon), and a quaternized polyvinylpyrrolidone derivative ("Gafquat 734", "Gafquat 755" and "Gafquat 755N", each product of ISP Japan).

Of these polymers, polysaccharide polymers are preferred, with natural polymer type ones having a cellulose skeleton or xanthan gum skeleton being more preferred. These polymers may be used either singly or in combination of two or more. Their content in the hair dye composition of the present invention is preferably from 0.1 to 10 wt. %, more preferably from 0.1 to 3 wt. % from the viewpoints of easiness in application work and reduced dripping. The hair dye composition of the present invention has a viscosity of preferably from 100 to 80000, more preferably from 300 to 50000 mPa·s from the viewpoints of easiness to apply and reduced dripping. The term "viscosity" as used herein is a value determined after rotating the composition for 1 minute at 6 rpm at 25° C. by using a Brookfield viscometer.

Although incorporation of a dye other than Component (A) in the hair dye composition of the present invention is not necessary, an oxidation dye intermediate (precursor or coupler) or a direct dye typically employed for hair dyes may be incorporated.

Examples of the precursor include paraphenylenediamine, toluene-2,5-diamine, 2-chloro-paraphenylenediamine, N-methoxyethylparaphenylenediamine, N,N-bis(2-hydroxyethyl)paraphenylenediamine, 2-(2-hydroxyethyl)paraphenylenediamine, 2,6-dimethylparaphenylenediamine, 4,4'-diaminodiphenylamine, 1,3-bis(N-(2-hydroxyethyl)-N-(4-aminophenyl)amino)-2-propanol, PEG-3,2,2'-paraphenylenediamine, paraminophenol, paramethylaminophenol, 3-methyl-4-aminophenol, 2-aminomethyl-4-aminophenol, 2-(2-hydroxyethylaminomethyl)-4-aminophenol, orthoaminophenol, 2-amino-5-methylphenol, 2-amino-6-methylphenol, 2-amino-5-acetamidophenol, 3,4-diaminobenzoic acid, 5-aminosalicylic acid, 2,4,5,6-tetraminopyrimidine, 2,5,6-triamino-4-hydroxypyrimidine, 4,5-diamino-1-(4'-chlorobenzyl)pyrazole and 4,5-diamino-1-hydroxyethylpyrazole, and salts thereof.

Examples of the coupler include metaphenylenediamine, 2,4-diaminophenoxyethanol, 2-amino-4-(2-hydroxyethylamino)anisole, 2,4-diamino-5-methylphenetole, 2,4-diamino-5-(2-hydroxyethoxy)toluene, 2,4-dimethoxy-1,3-diaminobenzene, 2,6-bis(2-hydroxyethylamino)toluene, 2,4-diamino-5-fluorotoluene, 1,3-bis(2,4-diaminophenoxy)propane, metaminophenol, 2-methyl-5-aminophenol, 2-methyl-5-(2-hydroxyethylamino)phenol, 2,4-dichloro-3-aminophenol, 2-chloro-3-amino-6-methylphenol, 2-methyl-4-chloro-5-aminophenol, N-cyclopentyl-metaminophenol, 2-methyl-4-methoxy-5-(2-hydroxyethylamino)phenol, 2-methyl-4-fluoro-5-aminophenol, resorcin, 2-methylresorcin, 4-chlororesorcin, 1-naphthol, 1,5-dihydroxynaphthalene, 1,7-dihydroxynaphthalene, 2,7-dihydroxynaphthalene, 2-isopropyl-5-methylphenol, 4-hydroxyindole, 5-hydroxyindole, 6-hydroxyindole, 7-hydroxyindole, 6-hydroxybenzomorpholine, 3,4-methylenedioxyphenol, 2-bromo-4,5-methylenedioxyphenol, 3,4-methylenedioxyaniline, 1-(2-hydroxyethyl)amino-3,4-methylenedioxybenzene, 2,6-dihydroxy-3,4-dimethylpyridine, 2,6-dimethoxy-3,5-diaminopyridine, 2,3-diamino-6-methoxypyridine, 2-methylamino-3-amino-6-methoxypyridine, 2-amino-3-hydroxypyridine, and 2,6-diaminopyridine and salts thereof.

When the oxidation dye intermediate is added to the hair dye composition of the present invention, the content thereof in a stock solution of aerosol is preferably from 0.01 to 20 wt. %, more preferably from 0.5 to 5 wt. %.

Examples of the direct dye include acid dyes, nitro dyes, disperse dyes, basic dyes and direct dyes described in JP-A-2003-342139. Examples of the acid dyes include Blue No. 1, Violet No. 401, Black No. 401, Orange No. 205, Red No. 227, Red No. 106, Yellow No. 203, and Acid Orange 3. Examples of the nitro dyes include 2-nitroparaphenylenediamine, 2-amino-6-chloro-4-nitrophenol, 3-nitro-p-hydroxyethylaminophenol, 4-nitroorthophenylenediamine, 4-amino-3-nitrophenol, 4-hydroxypropylamino-3-nitrophenol, HC Blue 2, HC Orange 1, HC Red 1, HC Yellow 2, HC Yellow 4, HC Yellow 5, HC Red 3, and N,N-bis-(2-hydroxyethyl)-2-nitro-paraphenylenediamine. Examples of the disperse dyes include Disperse Violet 1, Disperse Blue 1 and Disperse Black 9, while those of the basic dyes include Basic Blue 99, Basic Brown 16, Basic Brown 17, Basic Red 76, Basic Red 51, Basic Yellow 57, Basic Yellow 87 and Basic Orange 31.

When the direct dye is added to the hair dye composition of the present invention, the content of it therein is preferably from 0.001 to 5 wt. %, more preferably from 0.01 to 3 wt. %.

In the hair dye composition of the present invention, a surfactant may be incorporated further in order to improve dyeing properties and easiness in application work, and to provide good feel of the hair to the touch during or after the treatment. Examples of such a surfactant include anionic surfactants such as alkylbenzene sulfonates, alkyl or alkenyl ether sulfates, alkyl or alkenyl sulfates, olefin sulfonates, alkane sulfonates, saturated or unsaturated fatty acid salts, alkyl or alkenyl ether carboxylates, α-sulfone fatty acid salts, N-acylamino acid surfactants, phosphate mono- or di-ester surfactants and sulfosuccinates; amphoteric surfactants such as imidazoline, carbobetaine, amidobetaine, sulfobetaine, hydroxysulfobetaine and amidosulfobetaine amphoteric surfactants; nonionic surfactants such as polyoxyalkylene alkyl ethers, polyoxyalkylene alkenyl ethers, higher fatty acid sucrose esters, polyglycerin fatty acid esters, higher fatty acid monoethanolamides or diethanolamides, polyoxyethylene hydrogenated castor oils, polyoxyethylene sorbitan fatty acid esters, polyoxyethylene sorbitol fatty acid esters, alkyl saccharide surfactants, alkylamine oxides, and alkylamidoamine oxides; and cationic surfactants such as imidazoline ring-opened type quaternary ammonium salts, mono(long chain) alkyl quaternary ammonium salts and di(long chain)alkyl quaternary ammonium salts. Examples of the counterion of the anionic residue of the above-described surfactants include alkali metal ions such as sodium ion and potassium ion; alkaline earth metal ions such as calcium ion and magnesium ion, ammonium ions, alkanolamines having 1 to 3 alkanol groups with 2 or 3 carbon atoms (such as monoethanolamine, diethanolamine, triethanolamine and triisopropanolamine). Examples of the counterion of the cationic residue include halide ions such as chloride ions, bromide ions and iodide ions, methosulfate ions and saccharinate ions.

These surfactants may be used either singly or in combination of two or more. Their content in the hair dye composition of the present invention is preferably from 0.1 to 15 wt. %, more preferably from 1 to 10 wt. %.

In the hair dye composition of the present invention, an alkali agent typically employed for hair dyes can be incorporated. Examples of the alkali agent include aqueous ammonia, alkanolamines such as mono-, di- or triethanolamine, alkyl or aralkylamines such as butylamine and benzylamine, inorganic bases such as sodium hydroxide, potassium hydroxide, sodium carbonate and potassium carbonate, basic amino acids such as arginine, lysine and histidine, and salts such as guanidine carbonate, ammonium chloride and ammonium bicarbonate. Of these, monoethanolamine is preferred because of its dyeing power.

These alkali agents may be used either singly or in combination of two or more. Their content in the hair dye composition of the present invention is preferably from 0.01 to 20 wt. %, more preferably from 0.1 to 10 wt. % in order to dye the gray hair of Asian people into a desirable non-reddish black color.

In the hair dye composition of the present invention, an antioxidant commonly employed for hair dyes can be incorporated. Preferred examples of the antioxidant include sulfurous acid, ascorbic acid, thioglycolic acid, L-cysteine and N-acetyl-L-cysteine and salts thereof. Of these, ascorbic acid and salts thereof are preferred because it contributes to improvement of dyeing power as well as stabilization of Component (A).

The above-described antioxidants may be used either singly or in combination of two or more. Their content in the hair dye composition of the present invention is preferably from 0.01 to 2 wt. %, more preferably from 0.05 to 1 wt. % from the viewpoint of dyeing the gray hair of Asian people into a desirable non-reddish black color.

In the hair dye composition of the present invention, an oil agent can be incorporated further as a conditioning agent. Examples of the oil agent include hydrocarbons such as squalene, squalane, liquid paraffin, liquid isoparaffin, and cycloparaffin; glycerides such as castor oil, cacao oil, mink oil, avocado oil and olive oil; waxes such as beeswax, spermaceti, lanolin and carnauba wax; esters such as isopropyl palmitate, isopropyl myristate, octyldodecyl myristate, hexyl laurate, cetyl lactate, propylene glycol monostearate, oleyl oleate, hexadecyl 2-ethylhexanoate, isononyl isononanoate, and tridecyl isononanoate; higher fatty acids such as capric acid, lauric acid, myristic acid, palmitic acid, stearic acid, behenic acid, oleic acid, coconut oil fatty acid, isostearyl acid, and isopalmitic acid; higher alcohols such as myristyl alcohol, cetyl alcohol, stearyl alcohol, behenyl alcohol, 2-octyl-dodecanol, and cetostearyl alcohol; and other oil agents such as isostearyl glyceryl ether and polyoxypropylene butyl ether. Of these, higher alcohols are preferred, with myristyl alcohol, cetyl alcohol and stearyl alcohol being more preferred. These oil agents may be used either singly or in combination of two or more. Their content in the hair dye composition of the present invention is preferably from 0.2 to 2 wt. %, more preferably from 0.3 to 1.8 wt. %, even more preferably from 0.5 to 1.5 wt. %.

In the hair dye composition of the present invention, other components typically employed for hair dyes such as an aqueous medium, stabilizer, buffer, perfume, touch improver, chelating agent, solubilizing agent, preservative or the like may be added, depending on the purpose of the composition as needed.

The melanin precursor as Component (A) reacts with oxygen in the air under basic conditions and is converted into a melanin pigment. The hair dye composition of the present invention is therefore adjusted to a pH range from 8 to 11, preferably from 8.5 to 11.

The hair dye composition of the present invention is provided preferably in the form of an aerosol in order to maintain its dyeing power even after repeated use and to improve the dyeing power. In order to provide the composition in the aerosol form, it is only necessary to fill a pressure container (aerosol can or the like) with the hair dye composition of the present invention as an aerosol stock solution together with a propellant.

As the propellant, compressed gas and liquefied gas typically used for aerosol products are usable. Examples of the compressed gas include nitrogen gas, carbon dioxide gas, and argon gas, while those of the liquefied gas include liquefied petroleum gas, volatile $C_{3-5}$ hydrocarbons and dimethyl ether. Of these, nitrogen gas, liquefied petroleum gas and dimethyl ether are preferred. Two or more propellants may be used in combination. In order to attain an adequate injection speed, it is preferred to incorporate from 1 to 20 wt. %, more preferably from 3 to 15 wt. % of the propellant(s) in the total composition composed of the stock solution and propellant. In addition, it is preferred to control the internal pressure of the aerosol can after filling to fall within from 0.3 to 0.5 MPa (25° C.).

When the composition is filled in a container, clinching and deaeration are preferably carried out simultaneously to reduce the air remaining inside the container. Such a deaeration operation is effective for stabilizing the content in the container. The deaeration operation is performed preferably under a pressure not greater than 48 kPa.

The hair dye composition of the present invention can of course be used at room temperature, but has improved dyeing power when heat and oxygen are supplied by a drier.

EXAMPLES

Example 1 and Comparative Examples 1 and 2

An aerosol type one-part hair dye composition was obtained by preparing a stock solution of the aerosol type one-part hair dye composition in accordance with the formulation shown in Table 1, filling the stock solution in an aerosol test bottle (product of Tokyo Koubunshi Corporation), clinching the bottle, and filling with a nitrogen gas of 0.5 MPa as a propellant.

The aerosol type one-part hair dye compositions thus obtained were evaluated as described below for their dyeing properties. The results are shown in Table 1.

Dyeing Property (ΔE):

Each of the aerosol type one-part hair dye compositions (1 g) was applied to about 1 g of a bundle of dry white hair obtained from a Chinese woman. After the resulting hair bundle was left to stand for 5 minutes at room temperature, it was shampooed and washed with water. After repetition of the above-described dyeing operation three times, the dyeing property of the hair dye compositions on the white hair was evaluated (ΔE, Minolta CR300)

Hair Touch after Treatment

The hair dye composition was evaluated for the hair touch by five panelists. When the number of the panelists who rated the hair touch was good was three or more, the composition was evaluated as "good"; when the number was one or two, the composition was evaluated as "fair"; and when the number was zero, the composition was rated as "poor".

TABLE 1

| | | Formulation of stock solution (wt. %) | | |
|---|---|---|---|---|
| | Raw materials | Ex. 1 | Comp. Ex. 1 | Comp. Ex. 2 |
| (A) | Mixture of 5,6-dihydroxyindole and 5,6-dihydroxyindole-2-carboxylic acid (molar ratio: 90:10) | 0.3 | 0.3 | 0.3 |
| (B) | Mixture of low-viscosity dimethicone, highly polymerized dimethicone and aminoethylaminopropyl-methylpolysiloxane copolymer ("CF1046", product of Dow Corning Toray) | 3 | 3 | 0 |
| (C) | 1,3-Butylene glycol | 3 | 0 | 0 |
| Others | Polyoxyethylene tridecyl ether ("Softanol 90", product of Nippon Shokubai) | 1.5 | 1.5 | 1.5 |
| | Hydroxypropyl xanthan gum ("Rhaball gum EX", product of Dainippon Sumitomo Pharma) | 0.8 | 0.8 | 0.8 |
| | 95 vol. % Ethanol | 6 | 6 | 6 |
| | Monoethanolamine | 0.5 | 0.5 | 0.5 |
| | Ascorbic acid | 0.3 | 0.3 | 0.3 |
| | Sodium hydroxide | q.s. | q.s. | q.s. |
| | Purified water | Balance | Balance | Balance |
| Total | | 100 | 100 | 100 |
| pH | | 10 | 10 | 10 |
| Viscosity (mPa · s) at 25° C. | | 15000 | 15000 | 15000 |
| Evaluation | Dyeing property (ΔE) | 50 | 47 | 40 |
| | Hair touch after treatment | Good | Fair | Poor |

The invention claimed is:

1. A one-part hair dye composition comprising the following components (A) to (C):

(A) one or two or more compounds represented by the following formula (1):

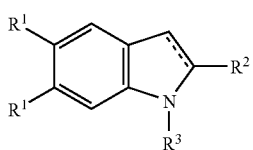

wherein, a broken line represents the presence or absence of a π bond, $R^1$ represents a hydroxyl or acetoxy group, $R^2$ represents a hydrogen atom, —COOR (R representing a hydrogen atom, methyl group or ethyl group) or —COO$^-$X$^+$ (X$^+$ representing a cation), and $R^3$ represents a hydrogen atom, acetyl group, methyl group or ethyl group, (B) a silicone in 0.01-10 wt % of said composition; and (C) a polyol, wherein the composition has a pH of from 8 to 11.

2. The one-part hair dye composition according to claim 1, wherein said Component (C) is one or more polyols selected from $C_{2-20}$ polyols.

3. The one-part hair dye composition according to claim 1 further comprising a monoethanolamine and having a pH of from 8.5 to 11.

4. The one-part hair dye composition according to any one of claims 1 to 3, further comprising an ascorbic acid or a salt thereof.

5. The one-part hair dye composition according to claim 2, further comprising a monoethanolamine and having a pH of from 8.5 to 11.

6. The one-part hair dye composition according to claim 5, further comprising an ascorbic acid or a salt thereof

* * * * *